(12) United States Patent
Muller

(10) Patent No.: US 6,652,903 B2
(45) Date of Patent: Nov. 25, 2003

(54) DRY-COPYING METHOD FOR PRODUCING FLAT, INDIVIDUALLY DOSED PREPARATIONS OF ACTIVE AGENTS

(75) Inventor: Walter Muller, Neuwied (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 10/163,752

(22) Filed: Jun. 6, 2002

(65) Prior Publication Data

US 2002/0182317 A1 Dec. 5, 2002

Related U.S. Application Data

(63) Continuation of application No. 09/743,231, filed as application No. PCT/EP99/04612 on Jul. 2, 1999.

(30) Foreign Application Priority Data

Jul. 9, 1998 (DE) .......................... 198 30 650

(51) Int. Cl.$^7$ .............................. B05D 3/02; B05D 7/04
(52) U.S. Cl. ...................... 427/2.14; 427/2.1; 427/2.15; 427/2.17; 427/2.23; 427/256; 427/258; 427/261; 427/265; 427/284; 427/285; 427/286; 427/288; 427/355; 427/359; 427/361; 427/266; 427/372.2; 427/375; 427/402; 427/421; 427/428
(58) Field of Search .................. 427/2.1, 2.14, 427/2.15, 2.17, 2.23, 256, 258, 261, 265, 284, 285, 286, 288, 355, 359, 361, 372.2, 375, 402, 421, 428

(56) References Cited

U.S. PATENT DOCUMENTS

| 3,877,413 A | | 4/1975 | Rowell et al. |
|---|---|---|---|
| 4,197,289 A | * | 4/1980 | Sturzenegger et al. ...... 424/443 |
| 5,268,259 A | | 12/1993 | Sypula |
| 5,768,675 A | | 6/1998 | Estabrooks |
| 5,930,569 A | | 7/1999 | Roof, Jr. et al. |
| 6,074,688 A | | 6/2000 | Pletcher et al. |
| 6,112,036 A | | 8/2000 | Shinohara |

FOREIGN PATENT DOCUMENTS

| DE | 032 04 582 U1 | 8/1983 |
|---|---|---|
| DE | 692 20 031 T 2 | 9/1997 |
| EP | 0 560 990 A1 | 9/1993 |
| WO | WO 92/14451 | 9/1992 |
| WO | WO 96/35516 | 11/1996 |
| WO | WO 96/39257 | 12/1996 |
| WO | WO 97/38480 | 10/1997 |
| WO | WO 98/20861 | 5/1998 |

* cited by examiner

*Primary Examiner*—Shrive P. Beck
*Assistant Examiner*—Jennifer Kolb Michener
(74) *Attorney, Agent, or Firm*—D. Peter Hochberg; Katherine R. Vieyra; Sean Mellino

(57) ABSTRACT

A method for metering active ingredient in powder form onto a predetermined area is characterized in that
 the active ingredient is transferred as electrically charged powder to a roll with the opposite charge,
 the active ingredient transferred to the roll is transferred to a two-dimensional substrate with an electric charge opposite to the active ingredient,
 the active ingredient transferred to the substrate is fixed by means of a heat treatment.

12 Claims, 1 Drawing Sheet

DRY-COPYING METHOD FOR PRODUCING FLAT, INDIVIDUALLY DOSED PREPARATIONS OF ACTIVE AGENTS

This application claims the benefit of U.S. patent application No. 09/743,231, filed Feb. 28, 2001, now abandoned, which is a 371 of PCT/EP99/04612, filed Jul. 2, 1999.

BACKGROUND OF THE INVENTION

1. Field of the Invention

Single-dose active ingredient preparations mean preparations which contain a predetermined amount of active substance in separate reaction units which can be handled individually.

An active ingredient for the purpose of this invention may be understood to be, for example, a medicinal substance, an insecticide, a pesticide, a reagent, etc.

2. Description of the Related Art

If an active substance names, for example, a medical active ingredient, such single-dose pharmaceutical forms are, for example, tablets, capsules, suppositories or transdermal therapeutic systems (TTS).

Non-single-dose pharmaceutical forms would be, for example, sprays, syrups, ointments and drops, with which the actual dosage takes place only immediately before use.

In single-dose active ingredient preparations, the active ingredient is to be processed in an appropriate amount together with any excipients necessary to give the active ingredient preparations ready for use. This technology can be regarded as mature for the production of tablets and capsules. Modern tablet presses and capsule-filling machines guarantee a high production rate and very accurate metering in the range 95–105% of the specification.

Transdermal therapeutic systems are still a relatively recent pharmaceutical form which is used externally in the form of a plaster on the skin and delivers the active ingredient through the skin to the body. Special metering techniques are used to produce these TTS, and further innovations in terms of new metering techniques are possible.

In one embodiment of these TTS, the active ingredient is contained directly in the adhesive and, during production, is metered together with the adhesive two-dimensionally onto a sheet.

This means that TTS are the only pharmaceutical form for which it is important to meter a medicinal active ingredient onto a predetermined area in a predetermined amount. Considering non-medicinal active ingredients such as, for example, insecticides, pesticides or reagents, two-dimensional preparations in the form of impregnated papers, sheets or boards have been known for a long time. However, the demands on the accuracy of metering in the area for these applications are not great.

SUMMARY OF THE INVENTION

The present invention is based on the object of providing a method for metering active ingredients in powder form onto a redetermined area.

This object is achieved with the use of the techniques known from the dry copying process by a method in which the active ingredient is transferred as electrically charged powder to a roll with the opposite charge, then the active ingredient is transferred from the roll to a two-dimensional substrate with an electric charge opposite to the active ingredient, and the active ingredient transferred to the substrate is fixed by means of a heat treatment.

It has emerged that this technique is capable of metering active ingredients in powder form onto an area with an accuracy sufficient for medicinal products. This is directly discernible with color copying, in which each color is metered separately, and major inaccuracies would result in wrong colors.

DETAILED DESCRIPTION OF THE INVENTION

Figure 1:
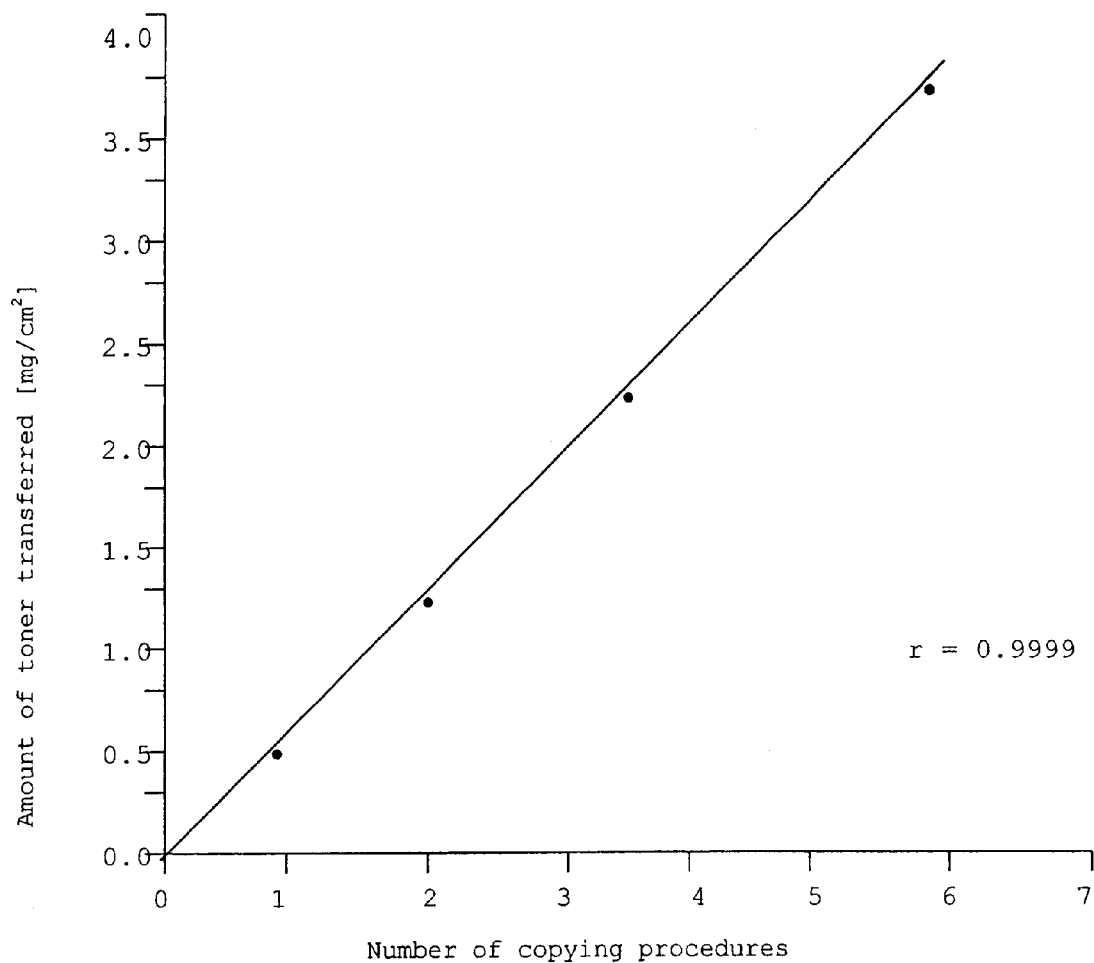
FIG. 1 is a graph showing the amount of toner proportional to the number of copying procedures.

The dry copying process or xerography functions in the manner described hereinafter.

A roll coated with a photoconductive material is provided with a positive electric charge and exposed through a suitable optical system to the original to be copied. Through this procedure, the charge is at least partially removed wherever the conductivity of the photoconductive material increases due to the exposure.

In a next step, negatively charged colored particles (toners) are applied to the roll, but these remain adherent only on the still charged areas of the roll in an amount depending on the size of the charge, and produce a visible image there.

Subsequently, the colored particles (toners) are transferred to a positively charged paper or sheet and fixed there b a heat treatment.

A modern variant of the method is employed in so-called laser printers. In this case, the roll is directly exposed to a laser beam without original, and thus the image is traced under computer control directly on the roll. Otherwise, the same technology is used for laser printers as for dry copiers.

The present invention is based on the use of these processes in order to transfer active ingredient particles, instead of the colored pigments, to paper or, in general, sheets.

Experiments were carried out with a normal black/white copier to find the amounts of toner which can be transferred to sheet and the reproducibility thereof.

Commercially available large polyester overhead sheets in the DIN A4 format are used as sheet. The original used was a dead-black sheet of paper, and the maximum degree of blackening was chosen for the copy. The results are recorded the following table.

TABLE 1

| Experiment number | Toner application (mg/cm$^2$) |
| --- | --- |
| 1 | 0.609 |
| 2 | 0.601 |
| 3 | 0.640 |
| 4 | 0.603 |
| 5 | 0.603 |
| 6 | 0.604 |
| Average | 0.610 |
| Rel. error (%) | 2.4 |

The results show that-although only a comparatively small amount of toner was transferred, this was with an accuracy suitable for medicinal applications, too.

In another experiment it was then found whether the amount can be eased by multiple metering.

The results are depicted in FIG. 1 and show that the transferred amount of toner is proportional to the number procedures.

This result shows that although the amount transferred in one copying process is small, this disadvantage can be overcome by multiple copying without the accuracy of metering suffering thereby.

The amount of toner or active ingredient transferred depends on the charged state of the copying roll and can be increased by applying a stronger charge than usual with copying machines.

If the active ingredient is metered without a special pattern, it is possible to dispense entirely with the exposure step. In this case, the copying roll does not have to consist of photoconductive material.

If the metering is to take place in a pattern, the exposure step and the use of a copying roll coated with a photoconductive material, for example selenium, is necessary. The exposure can in this case take place via an original or else via a laser with computer control. The variability is, of course, greatest with computer-controlled laser exposure.

It is to be assumed that most active ingredients are colorless. From this viewpoint, it is worthwhile to admix an indicator dye to the active ingredient and excipient mixture in powder form. This dye then permits, after appropriate calibration, direct measurement by optical methods of the amount of active ingredient transferred, and automatic correction of any deviations from the specification.

The flat substrate onto which the active ingredient is transferred can moreover consist in principle of any materials as long as it is flexible and suitable for withstanding the fixing procedure. It is conceivable in this connection that the material will be employed in the form of sheets or will be supplied from a roll. This material is then cut into smaller pieces during further processing and thus converted into the single-dose active ingredient preparation. An alternative possibility is for the material also to be perforated, in which case the dosage is predetermined by the perforation.

The invention has been described with particular emphasis on the preferred embodiments, but variations and modifications within the spirit and scope of the invention may occur to those skilled in the art to which the invention pertains.

What is claimed is:

1. Method for metering a medicinal or pesticidal active ingredient in powder form onto a two dimensional substrate in form of a sheet, comprising:

transferring the active ingredient as electrically charged powder in a metered amount having accuracy sufficient for medicinal products to predetermined areas of a roll with the opposite charge;

further transferring the active ingredient from the roll to a predetermined area of said substrate, the substrate having an electric charge apposite to the active ingredient; and fixing the active ingredient transferred to the predetermined area of the substrate for TTS application by means of a heat treatment, wherein said procedure comprising the steps of transferring, further transferring and fixing is performed at least twice to increase the amount of active ingredient transferred to said area.

2. Method according to claim 1, further comprising metering together excipients likewise in powder form with the active ingredient.

3. Method according to claim 2, further comprising having at least one excipient acting as a fixative.

4. Method according to claim 2, one excipient which is colored and using said excipient for optical determination of the amount of active ingredient.

5. Method according to claim 1, further comprising coating the roll with a photoconducting material.

6. Method according to claim 1, influencing the charge on the roll and thus the amount and/or the pattern or active ingredient transfer by exposure of the loaded roll.

7. Method according to claim 6, further comprising patterning the roll by exposure to a computer-controlled laser beam or to an optical image of an original pattern.

8. A method according to claim 4, and further including correcting the amount of the active ingredient from any deviation from the specification for the active ingredient.

9. Method for metering a medicinal or pesticidal active ingredient in powder form onto a predetermined area for TTS applications, comprising:

transferring the active ingredient as electrically charged powder, in a metered amount having accuracy sufficient for medicinal products to predetermined areas of a roll with the opposite charge;

further transferring the active ingredient from the roll to a two-dimensional substrate in form of a sheet with an electric charge opposite to the active ingredient; and fixing the active ingredient transferred to the two-dimensional substrate by means of a heat treatment to farm a product for TTS application.

10. Method according to claim 9, further comprising metering together excipients likewise in powder form with the active ingredient.

11. Method according to claim 10, providing one excipient which is colored and using said excipient for optical determination of the amount of active ingredient.

12. A method according to claim 11, and further and including correcting the amount of the active ingredient from any deviation from the specification for the active ingredient.

* * * * *